(12) United States Patent
Renken et al.

(10) Patent No.: US 7,683,007 B2
(45) Date of Patent: Mar. 23, 2010

(54) ADVANCES IN AMINATION CATALYSIS

(75) Inventors: Terry L. Renken, Conroe, TX (US); Matthew W. Forkner, Spring, TX (US)

(73) Assignee: Huntsman Petrochemicals LLC, The Woodlands, TX (US)

( * ) Notice: Subject to any disclaimer, the term of this patent is extended or adjusted under 35 U.S.C. 154(b) by 270 days.

(21) Appl. No.: 11/634,704

(22) Filed: Dec. 6, 2006

(65) Prior Publication Data

US 2008/0227632 A1 Sep. 18, 2008

Related U.S. Application Data

(62) Division of application No. 10/124,925, filed on Apr. 18, 2002, now Pat. No. 7,196,033.

(60) Provisional application No. 60/340,658, filed on Dec. 14, 2001.

(51) Int. Cl.
*B01J 23/00* (2006.01)

(52) U.S. Cl. .......... 502/352; 502/325; 502/330; 502/331; 502/337; 502/345; 502/349

(58) Field of Classification Search .......... 502/325, 502/330, 331, 337, 345, 349, 352
See application file for complete search history.

(56) References Cited

U.S. PATENT DOCUMENTS

| | | | |
|---|---|---|---|
| 3,151,115 A | 9/1964 | Moss et al. | 260/268 |
| 3,654,370 A | 4/1972 | Yeakey et al. | 260/584 |
| 4,152,353 A | 5/1979 | Habermann | 260/585 B |
| 4,153,581 A | 5/1979 | Habermann | 252/472 |
| 4,409,399 A | 10/1983 | Swift et al. | 564/473 |
| 4,621,158 A | 11/1986 | Hubert | |
| 5,003,107 A | 3/1991 | Zimmerman et al. | 564/475 |
| 5,367,112 A | 11/1994 | Franczyk | 562/526 |
| 5,449,821 A * | 9/1995 | Neumann et al. | 562/546 |
| 5,530,127 A | 6/1996 | Reif et al. | 544/106 |
| 5,608,113 A | 3/1997 | Becker et al. | 564/480 |
| 5,723,641 A | 3/1998 | Tam et al. | 556/13 |
| 5,916,838 A | 6/1999 | Wulff-Döring et al. | |
| 5,958,825 A | 9/1999 | Wulff-Doring | 502/300 |
| 5,986,138 A | 11/1999 | Satyavathi et al. | 564/402 |
| 6,037,295 A | 3/2000 | Satyavathi et al. | 502/84 |
| 6,046,359 A | 4/2000 | Wulff-Doring | 564/398 |
| 6,057,442 A | 5/2000 | Wulff-Doring et al. | 544/106 |
| 6,074,604 A | 6/2000 | Saito et al. | |
| 6,159,894 A | 12/2000 | Eisenhuth et al. | 502/308 |
| 6,534,441 B1 * | 3/2003 | Bartley et al. | 502/337 |

FOREIGN PATENT DOCUMENTS

| | | |
|---|---|---|
| DE | 2758769 | 12/1977 |
| EP | A 017651 | 4/1979 |
| GB | 2 006 773 | 5/1979 |
| JP | 56-005942 | 1/1981 |
| WO | WO 94/24091 | 10/1994 |
| WO | WO 96/01146 | 1/1996 |

OTHER PUBLICATIONS

Abstract of China Patent 1,031,663 to Liu et al.

* cited by examiner

*Primary Examiner*—Stanley Silverman
*Assistant Examiner*—Paul A. Wartalowicz

(57) ABSTRACT

Provided herein are catalysts useful in reductive amination, which include nickel, copper, zirconium and/or chromium, oxygen, and tin. The presence of the tin increases the selectivity of the catalyst in reductive aminations over the catalysts of the prior art.

5 Claims, No Drawings

US 7,683,007 B2

ADVANCES IN AMINATION CATALYSIS

CROSS-REFERENCES TO RELATED APPLICATIONS

This application is a divisional of co-pending patent application Ser. No. 10/124,925, filed Apr. 18, 2002, which claims priority to U.S. Provisional Application Ser. No. 60/340,658 filed Dec. 14, 2001, each of which is incorporated herein by reference.

TECHNICAL FIELD

This invention relates to catalysts useful in the preparation of amines by reductive amination. More particularly, it relates to catalysts and processes for their use in the production of amines from alcohols, ketones, and aldehydes. Catalysts according to the invention comprise new combinations of metallic components, which new combinations in such catalysts yield improved performance in a reductive amination process that employs the catalysts provided.

BACKGROUND

Strictly speaking, "reductive amination" refers to the reaction of an aldehyde or ketone with ammonia (or a primary or secondary amine) and hydrogen in the presence of a metallic hydrogenation catalyst to give a primary, secondary, or tertiary amine product. Primary and secondary alcohols also undergo the same reaction, except that hydrogen is not consumed in the reaction. It has been found in general that catalysts useful in reductive amination of aldehydes and ketones are also useful in the amination of alcohols, though the reduction of an alcohol in general requires considerably higher temperature.

Catalysts useful in reductive amination and alcohol amination processes have been the subject of a large volume of work by chemists, and the prior art is replete with patents concerning catalytic materials and/or processes using catalytic materials as the including the following U.S. Pat. Nos. 6,159,894; 6,057,442; 6,037,295; 6,046,359; 5,986,138; 5,958,825; 5,723,641; 5,367,112; and 4,152,353, as well as PCT International Applications WO 96/01146 and WO 94/24091. All patents and patent application publications mentioned herein are incorporated by reference thereto in their entirety.

Catalysts useful in reductive amination have often historically comprised metals such as Ni, Co, and Cu as the active component, and are sometimes referred to as hydrogenation/dehydrogenation catalysts because they are active in both types of reactions. Other elements from the Periodic Table of the Elements are frequently incorporated into the catalyst to optimally tailor the activity or selectivity of the catalyst for the particular process in which it is employed. U.S. Pat. Nos. 4,153,581; 4,409,399; 4,152,353 are descriptive of some of the more successful types of reductive amination catalysts. Habermann, in U.S. Pat. No. 4,153,581, discloses a method of preparing amines using a catalyst comprising from about 20 to about 90 percent cobalt, from about 8 to about 72 percent copper, and from about 1 to about 16 percent of a third component selected from the group consisting of iron, zinc, zirconium, and mixtures thereof. The catalyst of U.S. Pat. No. 4,153,581 is specified to comprise at least about 20 percent cobalt. Since cobalt is a relatively expensive metal, it is desirable for practical reasons to have at hand a catalyst useful in the reductive amination of alcohols, etc., which has equal or superior activity to cobalt-bearing catalysts at a reduced cost over the cobalt-bearing catalysts.

Reductive amination process conditions are typically used to make primary amines by reaction of an alcohol with ammonia. Good selectivity to the primary amine is usually achievable when reacting a secondary alcohol is the presence of excess ammonia over a suitable catalyst and under reaction conditions known to those skilled in the art. Primary alcohols as reactant, however, under the same conditions and catalyst give rise to lower primary amine selectivity, in favor of significantly higher secondary amine product and significantly higher undesirable "hydrogenolysis" by-products, especially at higher levels of alcohol conversion. The hydrogenolysis by-products are formed by reductive cleavage, or the formal addition of hydrogen across C—C, C—O, and C—N bonds.

In the case of the amination of diethylene glycol, the primary commercially-useful products are 2-aminoethoxyethanol, morpholine, and bis(aminoethyl)ether. By-products formed by hydrogenolysis reactions and related aminated hydrogenolysis by-products include: methane, carbon dioxide, ethylene glycol, ethanol, ethylamine, ethanolamine, ethylenediamine, 2-methoxyethanol, and 2-methoxyethylamine. Higher molecular weight by-products such as N-ethylmorpholine, N-aminoethylmorpholine, 2-(N-ethylaminoethoxy)ethanol, etc., are also formed under reaction conditions. The formation of these materials leads to lower yields of the desired products, and also complicates the purification process. A catalyst that yields less of these by-products attendant to the production of desired molecules is advantageous from a commercial perspective.

U.S. Pat. No. 4,152,353 discloses catalysts containing Ni (20-49%), Cu (36-79%), and Fe, Zn, and/or Zr (1-15%) useful in the conversion of alcohols to primary amines. U.S. Pat. No. 6,057,442 described catalysts containing Ni (14-70% as NiO), Cu (1-30% as CuO), and Zr (20-85% as $ZrO_2$), with $Al_2O_3$ and/or $MnO_2$ (0-10%), useful in the conversion of alcohols to amines. Examples in this patent give results in the amination of diethylene glycol to 2-aminoethoxyethanol and morpholine. However, the examples in these patents do not specify the selectivities to hydrogenolysis by-products. However, in our experience similar catalysts afford relatively high levels of hydrogenolysis by-products in the amination of diethylene glycol. In practice, the high levels of these by-products present yields inferior products, purification problems, and lower overall yields of the desired amine products. Thus, if catalysts with improved selectivities to the desired primary amines over prior art reductive amination catalysts were provided, such catalysts would represent a significant advance in the art, commensurate with the degree of reduction of by-product formation during their use and the cost to manufacture the catalyst.

SUMMARY OF THE INVENTION

One aspect of the present invention is a catalyst useful in reductive amination which comprises the elements nickel, copper, zirconium, tin, and oxygen. Another aspect of the invention is the use of such a catalyst in a reductive amination process.

In another aspect of the invention, there is provided a catalyst useful in reductive amination which comprises the elements nickel, copper, chromium, tin, and oxygen. Another aspect of the invention is the use of such a catalyst in a reductive amination process.

DETAILED DESCRIPTION

We have discovered that the inclusion of tin in catalysts useful in reductive amination results in reduction of the amounts of unwanted hydrogenolysis by-products produced during reductive amination. Use of the catalysts of the present invention increases the level of selectivity to the desired amine product and minimizes by-product formation. A catalyst according to one aspect of the invention and to which the addition of tin has shown a beneficial effect in this regard is a catalyst which contains tin, nickel, copper, chromium and oxygen. A catalyst according to a second aspect of the invention and to which the addition of tin has shown a beneficial effect in this regard is a catalyst which contains tin, nickel, copper, zirconium and oxygen. These discoveries have led us to believe that the presence of tin in general when added to a prior art catalyst useful in reductive amination that also contains nickel and copper will show similar beneficial effects.

Catalysts according to the invention are preferably prepared by a process comprising the steps of: 1) co-precipitating from an aqueous solution containing the metal ions desired to be present in the finished catalyst, as their carbonate salts; 2) rinsing the co-precipitated carbonates to remove impurities; 3) calcining the mixture of co-precipitated carbonates to yield a mixture of metal oxides; 4) activating the mixed metal oxides by reduction with hydrogen; and 5) formation of pellets or tablets useful for a fixed-bed process.

Catalysts according to the invention are useful in the amination of a wide range of mono-functional and polyfunctional alcohols having a wide range of molecular weights. Such alcohols include, without limitation, ethylene glycol, diethylene glycol, triethylene glycol, polyethylene glycols, and polypropylene glycols. Suitable polypropylene glycols for reductive amination with a catalyst according to the invention include those designated as JEFFOL® PPG-230, JEFFOL® PPG400, and JEFFOL® PPG-2000 which are available from Huntsman Corporation of The Woodlands, Tex.

The Animation Process

An amination process that uses a catalyst according to the invention is preferably carried out in a fixed-bed reactor in the presence of excess ammonia and hydrogen, both under pressure. In an alternative form of the invention, amines other than ammonia may be employed, such as methylamine, ethylamine, etc. Reductive amination processes generally known in the art which employ a catalyst may be used in conjunction with the catalysts of the present invention.

A process according to the invention which uses a catalyst provided in accordance with the invention is not limited to a confining set of conditions. The feed stream may be liquid, supercritical fluid, or gaseous, and the reaction product stream taken from the reaction zone may be liquid, supercritical fluid, or gaseous. It is not necessary that the feed stream and the reaction product stream be in the same physical state. The reactor design is also not narrowly critical. The feed thereto may be upflowing or downflowing, and design features in the reactor which optimize plug flow in the reactor may be employed.

The reactants may be fed as a stream, typically continuously, to the fixed bed of the catalyst. The solid catalyst is usually in the form of pellets, tablets, extrudates, spheres, etc. The active catalyst components can either be unsupported or deposited on a support material, as is known to those skilled in the art, such as alumina, silica, etc. The reaction occurs in the bed and thus the bed defines the reaction zone. The effluent from the bed or the reaction zone is also a stream comprising the unreacted components of the feed stream and the principal amine reaction products, plus a number of other amine compounds.

The conditions for reaction are also not narrowly limited. For example, the pressures for carrying out the process may range from about 1.90 MPa (300 psig) to about 27.5 MPa (4000 psig), more preferably from about 8 MPa to about 14 MPa. In addition, the process may typically be carried out at temperatures from about 120° C. to about 300° C., preferably from about 150° C. to about 250° C.

The following examples are intended for the purpose of illustrating this invention and should not be construed as being delimitive of the scope of the invention in any way. In order to make direct comparisons of the various catalysts evaluated, a specific set of reaction conditions was chosen. As is well known in the art, the product mixtures of any reaction process can be changed by varying such things as the feed mole ratio of reactants, product recycle, hydrogen concentration, feed space velocity, time on organics, temperature, and the like. The selection of these operating variables is dependent on the desired conversions, product selectivity, and desired production rate.

In the examples which follow, the catalysts were characterized by BET surface area using a Micromeritics single point flow instrument, by total pore volume ("TPV") using a Quantachrome mercury porosimeter instrument, and by tablet crush strength, using a Chatillon instrument.

In each of the diethylene glycol amination examples which follow, the 100 cc reactor was fully charged with the test catalyst. The catalyst bed was subjected to a 2 hr reactivation with hydrogen at 250° C. Diethylene glycol and ammonia were both continuously fed at 100 g/hr and hydrogen gas was fed at 2.1 l/hr (calibrated at 0° C. and 1 atm). Samples were taken at several temperatures after sufficient time elapsed for the reactor to have lined out to consistent conditions and product effluent. The "hot spot" reaction temperature was measured by thermocouple reading on the outer skin of the reactor. Reactor effluent samples were analyzed by GC using a capillary column and components wt %'s were determined. The following abbreviations were used to denote the following chemical species: EGME is ethylene glycol monomethyl ether; EDA is ethylenediamine; BAEE is bisaminoethylether; 2-aminoethoxyethanol is AEE, and DEG is diethylene glycol.

Catalyst Preparations

COMPARATIVE EXAMPLE 1

Catalyst containing Ni—Cu—Zr. At room temperature with efficient mixing, a solution consisting of 2908 g (10 mol) nickel (II) nitrate *6H$_2$O, 358 g (1.54 mol) copper (II) nitrate *2.5H$_2$O, and 279 g (0.37 mol) of 15% zirconium acetate solution and 5 liters of deionized water, was added over about 2 hours to a solution of 1410 g (13.3 mol) sodium carbonate in 5 liters of deionized water. The resulting slurry was filtered to remove the mother liquor and the solid was reslurried with 6 liters of deionized water and refiltered. The solid carbonate salt mixture was then dried in a vacuum oven at 110-150° C. overnight and then calcined (1° C./min ramp to 460° C.) to decompose the carbonates to the oxides. The resulting oxide was slurried with 4 liters of deionized water, filtered, reslurried with another 4 liters of deionized water, and refiltered. The washed oxide mixture was dried in a vacuum oven at 110-150° C. overnight. The dry powder was then mixed with 3 wt. % graphite and slugged into ½ inch diameter pellets.

The slugged pellets were then charged to a tube furnace for reduction. The charged reactor was flushed with nitrogen and heated to 250° C. Hydrogen at about 5 mol % was then introduced into the nitrogen stream. The reactor was maintained at these conditions until no water was observed condensing in the exiting gas stream. The hydrogen rate was increased and nitrogen rate decreased in increments over about 6 hours until pure hydrogen was being fed through the catalyst bed. The temperature was then held for 2 hours at 250° C., then increased to 325° C. and held overnight. The heat to the reactor was then turned off and the reactor cooled. The hydrogen feed was turned off and nitrogen feed was started to flush hydrogen from the reactor. After about an hour of flushing, air was introduced at about 5% in the nitrogen stream and an exotherm was observed to pass through the bed as some partial surface oxidation took place. These conditions were maintained overnight. With no apparent exotherm in the reactor, the air flow was then increased in increments and nitrogen decreased until pure air was fed through the catalyst bed. The catalyst was then discharged from the reactor and formed into ⅛ inch diameter by ⅛ inch length tablets using a Stokes 16-stage machine. The results of elemental analysis, BET surface area, mercury porosimetry, and crush strength testing are given in Table 1. Also given are the results of DEG amination studies.

| Comparative Example 1 Ni—Cu—Zr | | | | | | | |
|---|---|---|---|---|---|---|---|
| % Ni | % Cu | % ZrO$_2$ | % SnO | % Cr | SA (BET) | TPV (cc/g) | Ave. Crush (lb) |
| 81.6 | 13.4 | 5.0 | — | — | 30.0 | 0.106 | 15.0 |

| DEG Amination, Component Wt % In Reactor Effluent | | | | | |
|---|---|---|---|---|---|
| | Hot Spot Reaction Temp.(C°) | | | | |
| | 170° | 180° | 190° | 200° | 210° |
| EGME + EGME-Amine | 0.16 | 0.26 | 0.52 | 0.63 | 0.82 |
| EDA | 0.05 | 0.14 | 0.28 | 0.29 | 0.29 |
| Morpholine | 3.53 | 10.81 | 26.11 | 36.90 | 45.60 |
| BAEE | 0.34 | 0.93 | 1.53 | 1.81 | 1.83 |
| AEE | 23.07 | 34.37 | 34.13 | 29.94 | 24.69 |
| DEG | 70.70 | 47.69 | 26.67 | 16.36 | 11.59 |
| Heavies | 0.83 | 2.38 | 3.75 | 4.51 | 3.89 |
| % DEG conversion | 29.30 | 52.31 | 73.33 | 83.64 | 88.41 |

EXAMPLE 2

Catalyst containing Ni—Cu—Zr—Sn. This catalyst is similar in formulation to that described in Comparative Example 1, except that Sn was incorporated into the formulation using tin(IV) tetrachloride as reagent.

A metal salt solution was prepared, consisting of 2908 g (10 mol) nickel (II) nitrate *6H$_2$O and 358 g (1.54 mol) copper (II) nitrate *2.5H$_2$O, 301 g (0.40 mol) zirconium acetate (15% solution), 126 g (0.36 mol) tin tetrachloride, and 5 liters of deionized water. This solution and a base solution, consisting of 1415 g (13.4 mol) sodium carbonate and 5 liters of deionized water, were simultaneously added with efficient agitation to a reaction vessel at ambient temperature. The resulting precipitate was filtered, washed, dried, calcined, reduced and stabilized, and tabletted as described in Example 1. Results of elemental analysis, BET surface area, mercury porosimetry, and crush strength are given in Table 1. Also given are the results of DEG amination studies.

| Example 2 Ni—Cu—Zr—Sn | | | | | | | |
|---|---|---|---|---|---|---|---|
| % Ni | % Cu | % ZrO$_2$ | % SnO | % Cr | SA (BET) | TPV (cc/g) | Ave. Crush (lb) |
| 76.8 | 12.6 | 5.1 | 5.6 | — | 42.2 | 0.089 | 13.6 |

| DEG Amination, Component Wt % in Reactor Effluent | | | | | |
|---|---|---|---|---|---|
| | Hot Spot Reaction Temp.(C°) | | | | |
| | 170° | 180° | 190° | 200° | 210° |
| EGME + EGME-Am | 0.07 | 0.02 | 0.07 | 0.10 | 0.14 |
| EDA | 0.08 | 0.11 | 0.24 | 0.31 | 0.29 |
| Morpholine | 3.58 | 5.57 | 22.34 | 50.63 | 68.15 |
| BAEE | 0.84 | 2.27 | 5.40 | 4.96 | 2.74 |
| AEE | 25.46 | 36.79 | 35.61 | 16.22 | 2.88 |
| DEG | 67.82 | 50.71 | 22.03 | 5.62 | 0.36 |
| Heavies | 0.72 | 2.25 | 7.26 | 8.83 | 8.41 |
| % DEG conversion | 32.18 | 49.29 | 77.97 | 94.38 | 99.64 |

The catalyst of the invention embodied in Example 2 surprisingly gave significantly lower levels of the hydrogenolysis by-products EGME and EGME-amine at equivalent conversions than did the prior art catalyst of Comparative Example 1. Also surprising was the significantly higher levels of the desirable BAEE co-product. These positive effects are clearly ascribable to the presence of tin in the formulation. The Ni—Cu—Zr—Sn catalyst of this example was also found to be quite active in DEG amination.

COMPARATIVE EXAMPLE 3

Catalyst containing Ni—Cu—Zr. This catalyst, containing about 35% ZrO$_2$, was prepared using a similar procedure as in Comparative Example 1.

At room temperature with efficient mixing, a solution consisting of 4362 g (15 mol) nickel (II) nitrate *6H$_2$O, 537 g (2.31 mol) copper (II) nitrate *2.5H$_2$O, and zirconium acetate, 3386 g (15% solution, 4.5 mol) in 10 liters of deionized water, was added over about 2 hours to a solution of 2805 g (26.5 mol) sodium carbonate in 9 liters of deionized water. The resulting slurry was filtered and the solid washed by re-slurrying twice with 10 liters of fresh deionized water, followed by filtration. Subsequent catalyst preparation steps were identical to those described in Example 1. The resulting pelleted catalyst was analyzed and the results given in table 1. Also shown are the results of DEG amination studies.

| Comparative Example 3 Ni—Cu—Zr | | | | | | | |
|---|---|---|---|---|---|---|---|
| % Ni | % Cu | % ZrO$_2$ | % SnO | % Cr | SA (BET) | TPV (cc/g) | Ave. Crush (lb) |
| 55.7 | 9.3 | 35.1 | — | — | 66.6 | 0.086 | 16.7 |

| DEG Amination, Component Wt % in Reactor Effluent | | | | | |
|---|---|---|---|---|---|
| | Hot Spot Reaction Temp.(C°) | | | | |
| | 170° | 180° | 190° | 200° | 210° |

-continued

| | | | | | |
|---|---|---|---|---|---|
| EGME + EGME-Am | 0.11 | 0.24 | 0.43 | 0.68 | 0.75 |
| EDA | 0.03 | 0.09 | 0.20 | 0.29 | 0.26 |
| Morpholine | 1.99 | 7.30 | 16.05 | 29.92 | 29.43 |
| BAEE | 0.15 | 0.49 | 0.99 | 1.42 | 1.43 |
| AEE | 18.09 | 29.05 | 34.91 | 32.70 | 33.15 |
| DEG | 78.70 | 59.56 | 40.46 | 24.04 | 25.33 |
| Heavies | 0.13 | 1.00 | 2.33 | 3.09 | 2.08 |
| % DEG conversion | 21.30 | 40.44 | 59.54 | 75.96 | 74.67 |

Results of DEG amination with the Ni—Cu—Zr catalyst of Comparative Example 3 were found to be similar to that of Comparative Example 1, both in catalyst activity and selectivity.

EXAMPLE 4

Catalyst containing Ni—Cu—Zr—Sn. This catalyst was similar in composition to the catalyst in Comparative Example 3, except that about 5% SnO was incorporated into the catalyst using small mesh SnO powder.

A metal salt solution was prepared, consisting of 1454 g (5 mol) nickel (II) nitrate *6H$_2$O and 179 g (0.77 mol) copper (II) nitrate *2.5H$_2$O, 1129 g (1.50 mol) zirconium acetate (15% solution) and 3.5 liter deionized water. This solution was added over 2 hr to a well agitated slurry composed of 935 g (8.8 mol) of sodium carbonate, 29 g (0.21 mol) tin II oxide, and 3 liters of deionized water. The resulting precipitate was filtered, washed, dried, calcined, reduced and stabilized, and tabletted as described in Example 1. Results of elemental analysis, BET surface area, mercury porosimetry, and crush strength are given in Table 1. Also given are the results of DEG the amination studies.

Example 4 Ni—Cu—Zr—Sn

| % Ni | % Cu | % ZrO$_2$ | % SnO | % Cr | SA (BET) | TPV (cc/g) | Ave. Crush (lb) |
|---|---|---|---|---|---|---|---|
| 52.8 | 8.8 | 33.3 | 5.1 | — | 67.1 | 0.080 | 20.2 |

DEG Amination, Component Wt % in Reactor Effluent

| | Hot Spot Reaction Temp.(C°) | | | | |
|---|---|---|---|---|---|
| | 170° | 180° | 190° | 200° | 210° |
| EGME + EGME-Am | 0.00 | 0.13 | 0.07 | 0.12 | 0.18 |
| EDA | 0.01 | 0.03 | 0.22 | 0.36 | 0.42 |
| Morpholine | 0.06 | 4.13 | 13.73 | 36.77 | 58.50 |
| BAEE | 0.01 | 1.09 | 2.86 | 4.93 | 4.38 |
| AEE | 4.44 | 30.84 | 39.45 | 29.01 | 12.77 |
| DEG | 95.15 | 61.03 | 35.75 | 13.04 | 2.76 |
| Heavies | 0.14 | 1.11 | 3.44 | 5.82 | 6.26 |
| % DEG conversion | 4.85 | 38.97 | 64.25 | 86.96 | 97.24 |

Again, surprisingly, the selectivity to the hydrogenolysis by-products EGMA and EGME-Arm are low as compared to that obtained with the catalyst of Comparative Example 3. The level of the desirable BAEE co-product is also significantly higher with the Sn-containing catalyst of Example 4. The improved selectivities is attributed by the presence of the Sn.

COMPARATIVE EXAMPLE 5

The preparation of this Ni—Cu—Cr catalyst has been described in U.S. Pat. No. 3,037,025 (Texaco, Godfrey) and U.S. Pat. No. 3,151,115 (Texaco, Moss & Godfrey). The material used in this experiment was supplied by a commercial vendor using similar procedures. The results of DEG amination studies are given below.

Example 5 Ni—Cu—Cr

| % Ni | % Cu | % ZrO$_2$ | % SnO | % Cr | SA (BET) | TPV (cc/g) | Ave. Crush (lb) |
|---|---|---|---|---|---|---|---|
| 72.0 | 12.0 | — | — | 2.0 | 25.0 | 0.090 | 25.0 |

DEG Animation, Component Wt % in Reactor Effluent

| | Hot Spot Reaction Temp.(C°) | | | | |
|---|---|---|---|---|---|
| | 180° | 190° | 200° | 210° | 220° |
| EGME + EGME-Am | 0.13 | 0.21 | 0.37 | 0.70 | 1.08 |
| EDA | 0.01 | 0.20 | 0.06 | 0.13 | 0.19 |
| Morpholine | 1.19 | 3.22 | 9.51 | 23.52 | 42.67 |
| BAEE | 0.13 | 0.38 | 0.81 | 1.32 | 1.50 |
| AEE | 14.57 | 23.26 | 32.44 | 33.07 | 22.43 |
| DEG | 83.41 | 71.47 | 52.76 | 31.14 | 15.15 |
| Heavies | 0.04 | 0.18 | 1.29 | 3.72 | 5.83 |
| % DEG conversion | 16.59 | 28.53 | 47.24 | 68.86 | 84.85 |

The results of the DEG amination study using the Ni—Cu—Cr catalyst of Comparative Example 5 show the relatively high levels of the undesirable EGME and EGME-Amine hydrogenolysis by-products.

COMPARATIVE EXAMPLE 6

Catalyst containing Ni—Cu—Cr. At room temperature with efficient mixing, a solution consisting of 2326 g (8 mol) nickel (II) nitrate *6H$_2$O, 462 g (1.23 mol) copper (II) nitrate *2.5H$_2$O, and 194 g (0.48 mol) chromium nitrate *9H$_2$O in 5.0 liters of deionized water, was added over about 2 hours to a solution of 1161 g (11.0 mol) sodium carbonate in 5.0 liters of deionized water. The resulting precipitate was filtered, washed, dried, calcined, reduced and stabilized, and tabletted essentially as described in Example 1. Results of elemental analysis, BET surface area, mercury porosimetry, and crush strength are given in Table 1. Also given are the results of DEG amination studies.

Comparative Example 6 Ni—Cu—Cr

| % Ni | % Cu | % ZrO$_2$ | % SnO | % Cr | SA (BET) | TPV (cc/g) | Ave. Crush (lb) |
|---|---|---|---|---|---|---|---|
| 81.6 | 13.4 | — | — | 5.0 | 10.1 | 0.106 | 11.0 |

DEG Animation, Component Wt % in Reactor Effluent

| | Hot Spot Reaction Temp.(C°) | | | | |
|---|---|---|---|---|---|
| | 190° | 200° | 210° | 220° | 230° |
| EGME + EGME-Am | 0.04 | 0.07 | 0.19 | 0.31 | 0.74 |
| EDA | 0.00 | 0.01 | 0.03 | 0.07 | 0.11 |
| Morpholine | 0.52 | 1.49 | 5.63 | 14.15 | 39.75 |
| BAEE | 0.17 | 0.49 | 1.06 | 1.70 | 1.90 |
| AEE | 13.61 | 21.79 | 32.14 | 38.48 | 27.71 |
| DEG | 85.36 | 75.49 | 59.06 | 40.36 | 16.60 |
| Heavies | 0.00 | 0.00 | 0.18 | 1.14 | 3.42 |
| % DEG conversion | 14.64 | 24.51 | 40.94 | 59.64 | 83.40 |

The results of the DEG amination study using the Ni—Cu—Cr catalyst of Comparative Example 6 show the relatively high levels of the undesirable EGME and EGME-Amine hydrogenolysis by-products. The activity of this catalyst was also found to be low.

EXAMPLE 7

Catalyst containing Ni—Cu—Cr—Sn. This catalyst was formulated to be similar to that in Comparative Example 6, except that Sn was incorporated into the catalyst using tin (IV) chloride reagent.

A metal salt solution was prepared, consisting of 2326 g (8 mol) nickel (II) nitrate *$6H_2O$ and 462 g (1.23 mol) of a commercial 50% copper (II) nitrate solution, 206 g (0.52 mol) chromium nitrate *$9H_2O$, 92 g (0.26 mol) tin (IV) chloride *$5H_2O$ and 5 liters of deionized water. This solution and a base solution, consisting of 1166 g (11.0 mol) sodium carbonate in 5 liters of deionized water, were simultaneously added to a well agitated precipitation vessel at room temperature. The addition rates were adjusted to keep the pH between 7 and 10, the addition taking place over about 2 hours. The resulting slurry was filtered and the metal carbonate precipitate mixture re-slurried with 6 liters of fresh deionized water and then re-filtered. The solid carbonate salt mixture was then dried in a vacuum oven at 110-150° C. overnight and then calcined (1° C./min ramp to 460° C.) to decompose the carbonates to the oxides. The resulting oxide was slurried with 4 liters of deionized water, filtered, re-slurried with another 4 liters of deionized water, and re-filtered. The washed oxide mixture was dried in a vacuum oven at 110-150° C. overnight. The dry powder was then mixed with 3 wt % graphite and slugged into ½ inch diameter pellets.

The slugged pellets were then charged to a tube furnace for reduction and stabilization using a similar procedure to that outlined in Comparative Example 1. The catalyst slugs were then discharged from the reactor, ground to powder, and formed into ⅛ inch diameter by ⅛ inch length tablets using a Stokes 16-stage machine. The results of elemental analysis, BET surface area, mercury porosimetry, and crush strength are given in Table 1. Also given are the results of the DEG amination studies.

| Example 7 Ni—Cu—Cr—Sn | | | | | | | |
|---|---|---|---|---|---|---|---|
| % Ni | % Cu | % $ZrO_2$ | % SnO | % Cr | SA (BET) | TPV (cc/g) | Ave. Crush (lb) |
| 77.2 | 12.6 | — | 5.1 | 5.0 | 28.3 | 0.130 | 5.3 |

| DEG Amination, Component Wt % in Reactor Effluent | | | | | |
|---|---|---|---|---|---|
| | Hot Spot Reaction Temp.(C°) | | | | |
| | 180° | 190° | 200° | 210° | 220° |
| EGME + EGME-Am | 0.03 | 0.06 | 0.12 | 0.22 | 0.31 |
| EDA | 0.02 | 0.08 | 0.15 | 0.19 | 0.17 |
| Morpholine | 2.00 | 8.06 | 22.32 | 46.83 | 63.57 |
| BAEE | 0.62 | 2.02 | 4.03 | 4.69 | 3.33 |
| AEE | 21.78 | 33.30 | 34.00 | 19.96 | 6.68 |
| DEG | 74.42 | 51.80 | 27.42 | 8.31 | 1.35 |
| Heavies | 0.27 | 1.94 | 5.22 | 7.53 | 8.40 |
| % DEG conversion | 25.58 | 48.20 | 72.58 | 91.69 | 98.65 |

The catalyst of Example 7 was found to give significantly lower EGME and EGME-Amine hydrogenolysis by-products, and significantly higher of the desirable BAEE co-product over the catalyst of Comparative Examples 5 and 6. Again, increased selectivity is attributable to the presence of Sn.

Examples 8 and 9 below show amination results of polypropylene glycols JEFFOL® PPG-230 and JEFFOL® PPG-2000 respectively, using the Ni—Cu—Zr—Sn catalyst of this invention prepared in accordance with Example 2. The reactor employed for Examples 8 and 9 is a 100 cc tubular reactor, using 100 g/hr of DEG, 100 g/hr of ammonia, 0.5 mol/hr $H_2$ and operated at 2000 psi. Samples were taken after conditions stabilized for 2 hours, then stripped of water and lights, and titrated to determine the extent of the amination achieved.

| Example 8 Ni—Cu—Zr—Sn | | | | | | | |
|---|---|---|---|---|---|---|---|
| % Ni | % Cu | % $ZrO_2$ | % SnO | % Cr | SA (BET) | TPV (cc/g) | Ave. Crush (lb) |
| 76.8 | 12.6 | 5.1 | 5.6 | — | 42.2 | 0.089 | 13.6 |

| JEFFOL ® PPG-230 Amination | | | | |
|---|---|---|---|---|
| | Hot Spot Reaction Temp.(C°) | | | |
| | 180° | 190° | 200° | 210° |
| Total acetylatables, meq/g | 8.70 | 8.71 | 8.80 | 8.68. |
| Total Amine, meq/g | 6.71 | 7.90 | 8.41 | 8.47 |
| Primary Amine, meq/g | 6.70 | 7.89 | 8.40 | 8.42 |
| % conversion | 77.1 | 90.7 | 95.7 | 97.5 |
| % Primary Amine | 99.9 | 99.9 | 99.8 | 99.4 |

| Example 9 Ni—Cu—Zr—Sn | | | | | | | |
|---|---|---|---|---|---|---|---|
| % Ni | % Cu | % $ZrO_2$ | % SnO | % Cr | SA (BET) | TPV (cc/g) | Ave. Crush (lb) |
| 76.8 | 12.6 | 5.1 | 5.6 | — | 42.2 | 0.089 | 13.6 |

| JEFFOL ® PPG-2000 Amination | | | | |
|---|---|---|---|---|
| | Hot Spot Reaction Temp.(C°) | | | |
| | 180° | 190° | 200° | 210° |
| Total acetylatables, meq/g | 1.009 | 1.015 | 1.001 | 1.009 |
| Total Amine, meq/g | 0.738 | 0.891 | 0.955 | 0.975 |
| Primary Amine, meq/g | 0.734 | 0.889 | 0.953 | 0.973 |
| % conversion | 73.1 | 87.8 | 95.4 | 96.6 |
| % Primary Amine | 99.5 | 99.7 | 99.8 | 99.8 |

The polyols of Examples 8 and 9 contain secondary alcohol groups. In these examples, the primary amine selectivities were >99%, even at the high conversions of >95%. This is in contrast to the DEG amination Examples 1 through 7, which show the high production of secondary amines, which include morpholine and heavies.

The results of Examples 8 and 9 demonstrate the high activity and primary amine selectivity of the Sn-containing catalyst of this invention in polypropylene glycol aminations.

Although the catalytic compositions of the present invention have been described as being non-supported catalysts, the present invention also contemplates deposition of the metallic components of the catalyst compositions onto support materials known to those skilled in the art, using techniques which are well-known in the art, including without limitation, known forms of alumina, silica, charcoal, carbon, graphite, clays, mordenites, and molecular sieves, to provide supported catalysts as well.

Various aldehydes, ketones, and alcohols may be used as a starting raw material for a reductive amination process according to the invention, as the use of such starting materials is well-known in the art of reductive amination. In the case of alcohols, the alcohols useful as raw materials in a process according to the invention may be any primary or secondary alcohol. The alcohols known as JEFFOL® PPG-230, JEFFOL® D-230, JEFFOL® PPG400, JEFFOL® D-2000 available from Huntsman Corporation of The Woodlands, Tex. aminate well using the catalysts of the invention.

Various amines, including ammonia itself, may be used as a starting raw material for a reductive amination process according to the invention, as the use of such starting materials is well-known to those skilled in the art of reductive amination. Particularly useful are the organic amines, which term includes all primary and secondary amines known to be useful in reductive amination processes by those skilled in the art, and include without limitation, alkylamines, arylamines, alkylaryl amines, and polyalkylenepolyamines.

Consideration must be given to the fact that although this invention has been described and disclosed in relation to certain preferred embodiments, obvious equivalent modifications and alterations thereof will become apparent to one of ordinary skill in this art upon reading and understanding this specification and the claims appended hereto. Accordingly, the presently disclosed invention is intended to cover all such modifications and alterations, and is limited only by the scope of the claims which follow.

What is claimed is:

1. A catalyst useful in a reductive animation process for producing amines from alcohols, aldehydes, or ketones, wherein said catalyst consists of nickel, copper, tin, zirconium, and oxygen.

2. A catalyst according to claim 1 wherein the amount of tin in said catalyst is any amount between 0.20% and 20.00% by weight based upon the total weight of said catalyst, including every hundredth percentage therebetween.

3. A catalyst according to claim 2 wherein the amount of tin in said catalyst is any amount between 1.00% and 7.00% by weight based upon the total weight of said catalyst, including every hundredth percentage therebetween.

4. A catalyst useful in reductive amination consisting of:
a) nickel, present in any amount between 40.0 and 90.0% by weight based upon the total catalyst weight;
b) copper, present in any amount between 4.0 and 40.0% by weight based upon the total catalyst weight;
c) tin, present in any amount between 0.20 and 20.0% by weight based upon the total catalyst weight;
d) zirconium, present in any amount between 1.0 and 50.0% by weight based upon the total catalyst weight; and
e) oxygen, present in any amount between 3.0 and 25.0% by weight based upon the total catalyst weight.

5. A catalyst useful in reductive amination consisting of:
a) nickel, present in any amount between 60.0 and 80.0% by weight based upon the total catalyst weight;
b) copper, present in any amount between 6.0 and 14.0% by weight based upon the total catalyst weight;
c) tin, present in any amount between 1.0 and 7.0% by weight based upon the total catalyst weight;
d) zirconium, present in any amount between 3.0 and 25.0% by weight based upon the total catalyst weight; and
e) oxygen, present in any amount between 5.0 and 10.0% by weight wherein all percentages are based upon the total weight of the finished catalyst.

* * * * *